United States Patent [19]

Schell et al.

[11] Patent Number: 5,633,442
[45] Date of Patent: May 27, 1997

[54] METHOD OF PRODUCING PATHOGEN-RESISTANT PLANTS

[75] Inventors: Jeff Schell; Jürgen Logemann; Guido Jach, all of Köln, Germany; John Mundy, Copenhagen, Denmark

[73] Assignee: Max-Planck-Gesellschaft zur Forderung der Wissenschaften e.v., Germany

[21] Appl. No.: 375,186

[22] Filed: Jan. 18, 1995

Related U.S. Application Data

[63] Continuation of Ser. No. 215,163, Mar. 21, 1994, abandoned, which is a continuation of Ser. No. 810,390, Dec. 19, 1991, abandoned.

[30] Foreign Application Priority Data

Dec. 20, 1990 [DE] Germany .................. 40 40 954.6

[51] Int. Cl.$^6$ .................. C12N 15/09; C12N 15/29; C12P 1/04; A01H 1/00; A01H 5/00
[52] U.S. Cl. .................. 800/205; 800/DIG. 52; 435/172.3; 435/69.1; 435/320.1; 435/252.3; 536/23.2; 536/23.6; 935/18; 935/23
[58] Field of Search .................. 435/6, 172.1, 172.3, 435/252.3, 320.1; 800/200, 205, 255, DIG. 43, DIG. 52; 536/23.2, 23.6; 935/18, 23; 47/58.07

[56] References Cited

U.S. PATENT DOCUMENTS

| P.P. 412 | 7/1940 | Rosenberg | Plt./100 |
| 5,126,324 | 6/1992 | Clark et al. | 514/12 |

FOREIGN PATENT DOCUMENTS

| 0298918 | 1/1989 | European Pat. Off. . |
| 0375091 | 6/1990 | European Pat. Off. . |
| 9012097 | 10/1990 | WIPO . |

OTHER PUBLICATIONS

Hahlbrock, K. & Griesbach, H., *Ann. Rev. Plant Physiol.*, 30, (1979), pp. 105–130.
Darvill, A.G. & Albersheim, P., *Ann. Rev. Plant Physiol.*, 35, (1984), pp. 243–275.
Stirpe et al., *Brochem. J.*, 216, (1983), pp. 617–625.
Asano et al., *Carlsberg Ress. Commun.*, vol. 51, (1986), pp. 129–141.
Roberts, W. K. & Selitrennikoff, C.P., Biochimica et Biophysica Acta, 880, (1986), pp. 161–170.
Jun, Wang, Chemical Abstracts 113:12772, "Preparation of transgenic plants for control of virosis" (1990).
Asano et al., Carlsberg Res. Commun. 51, 129–141 (1986).
Leah et al., The Journal of Biological Chemistry, 266, 1564–1573 (1991).
Ebert et al., Bioconjugate Chemistry, 1, 331–336 (1990).
Sverdsen et al. 1982. Carlsberg Res. Commun. 47: 45–53.
Sanchez–Serrano et al. 1987. The EMBO Journal. 6(2): 303–306.
Thornburg et al. 1987. Proc. Natl. Acad. Sci. USA. 84: 744–748.
Leah et al. 1989. Plant Molecular Biology. 12: 673–682.
Potrykus. 1991. Ann. Rev. Plant Physiol. Plant Mol. Biol. 42: 205–225.
Goeddel et al. 1979. Nature. 281: 544–548.
Watson et al. 1992. Recombinant DNA. pp. 454–455.

*Primary Examiner*—Erich E. Veitenheimer
*Attorney, Agent, or Firm*—Brumbaugh, Graves, Donohue & Raymond

[57] ABSTRACT

Described are a method of producing pathogen-resistant plants in which a protein-synthesis inhibitor gene or a fusion product of the protein-synthesis inhibitor gene or of the protein-synthesis inhibitor protein with ligands permitting specific attachment to cells is introduced into the genotype of plants under the control of an active promotor, and the use of the protein-synthesis inhibitor protein obtained by introducing the protein-synthesis inhibitor gene into the bacterial overproducers for making pharmaceutical preparations.

6 Claims, 12 Drawing Sheets

```
CTTAATAGCACATCTTGTCCGTCTTAGCTTTGCATTACATCCATGGGGCAAAGATGGCG      60
                                              *          M  A  A  K  M  A
                                                        -1   1

AAGAACCTGGACAAGCCGCTCTTCACCGCGACGTTCAACGTTCAGGCCAGCTCCGCCGAC    120
 K  N  V  D  K  P  L  F  T  A  T  F  N  V  Q  A  S  S  A  D
               10                     20

TACGCCACCTTCATCGCCGGCATCCGCAACAAGCTCCGCAACCCGGCCCACTTCTCCCAC    180
 Y  A  T  F  I  A  G  I  R  N  K  L  R  N  P  A  H  F  S  H
               30                     40

AACCGCCCCGTGCTGCCCCCGGTCGAGCCCAACGTCCCCGCCGAGCAGGTGGTTCCACGTC   240
 N  R  P  V  L  P  P  V  E  P  N  V  P  P  S  R  W  F  H  V
               50                     60

GTGCTCAAGGCCTCCCCGACCAGCGCCGGGCTCACGCTGGCCATTCGGGCGACAACATC    300
 V  L  K  A  S  P  T  S  A  G  L  T  L  A  I  R  A  D  N  I
               70                     80

TACCTGGAGGGCTTCAAGAGCAGCGACGGCACCTGGTGGGAGCTCACCCCGGGCCTCATC    360
 Y  L  E  G  F  K  S  S  D  G  T  W  W  E  L  T  P  G  L  I
               90                    100

CCCGGCGCCACCTACGTCGGGTTCGGCGGCACCTACCGCGACCTTCTCGGCGACACCGAC    420
 P  G  A  T  Y  V  G  F  G  G  T  Y  R  D  L  L  G  D  T  D
              110                    120

AAGCTGACCAACGTCGCTCTCGGCCGGCAGCAGCTGGCGGACGCGGTGACCGCCCTCCAC    480
 K  L  T  N  V  A  L  G  R  Q  Q  L  A  D  A  V  T  A  L  H
              130                    140
```

FIG. 3A

```
GGGCGCACCAAGGCCGACAAGCCGTCCGGCCCGAAGCAGCAGGCGAGGAGGCGGTG      540
 G  R  T  K  A  D  K  P  S  G  P  K  Q  Q  A  R  E  A  V
                   150                      160

ACGACGCTGCTCCTCATGGTGAACGAGGCCACGCGGTTCCAGACGGTGTCTGGGTTCGTG  600
 T  T  L  L  M  V  N  E  A  T  R  F  Q  T  V  S  G  F  V
      170                      180

GCCGGGTTGCTGCACCCCAAGGCGGTGGAGAAGAAGAGCGGGAAGATCGGCAATGAGATG  660
 A  G  L  L  H  P  K  A  V  E  K  K  S  G  K  I  G  N  E  M
             190                      200

AAGGCCCAGGTGAACGGGTGGCAGGACCTGTCCGCGGCGCTGCTGAAGACGGACGTGAAG  720
 K  A  Q  V  N  G  W  Q  D  L  S  A  A  L  L  K  T  D  V  K
                   210                      220

CCTCCGCCCGGAAAGTCGCCAGCGAAGTTCGCGCCGATCGAGAAGATGGGCGTGAGGACG  780
 P  P  P  G  K  S  P  A  K  F  A  P  I  E  K  M  G  V  R  T
      230                      240

CTGTACAGGCCGCCAACACGCTGGGGATCCTGCTGTTCGTGGAGGTGCCGGGTGGGTTG   840
 A  V  Q  A  A  N  T  L  G  I  L  L  F  V  E  V  P  G  G  L
             250                      260

ACGGTGGCCAAGGCGCTGGAGCTGTTCCATGCGAGTGGGGAAATAGGTAGTTTTCCAG    900
 T  V  A  K  A  L  E  L  F  H  A  S  G  G  K  *

GTATACCTGCATGGTAGTGTAAAAGTCGAATAAACATGTCACAGAGTGACGGACTGATA   960

TAAATAAATAAACGTGTCACAGAGTTACATATAAACAAATAATAAATAATTAAAA      1020

ATGTCCAGTTTA₄₇                                                1078
```

FIG. 3B

```
GCGGTGACGACGCTGCTCCTCATGGTGAACGAGGCCACGCGGTTCCAGACGGTGTCGGGG          60
 A  V  T  T  L  L  L  M  V  N  E  A  T  R  F  Q  T  V  S  G
                      170                     180

TTCGTGGCCGGGCTGCTGCACCCCAAGGCGGTGGAGAAGAAGAGCGGGAAGATCGGCAAT         120
 F  V  A  G  L  L  H  P  K  A  V  E  K  K  S  G  K  I  G  N
                      190                     200

GAGATGAAGGCCCAGGTGAACGGGTGGCAGGACCTGTCCGCGGCGCTGCTGAAGACGGAC         180
 E  M  K  A  Q  V  N  G  W  Q  D  L  S  A  A  L  L  K  T  D
                      210                     220

GTGAAGCCCCCCGGCCCGGGAAAGTCGCCCAGCGAAGTTCACGCCCGATCGAGAAGATGGGCGTG    240
 V  K  P  P  P  G  K  S  P  A  K  F  T  P  I  E  K  M  G  V
                      230                     240

AGGACTGCTGAGCAGGCTGCCGCTACTTTGGGGATCCTGCTGTTCGTTGAGGTGCCGGGT         300
 R  T  A  E  Q  A  A  A  T  L  G  I  L  L  F  V  E  V  P  G
                      250                     260

GGGTTGACGGTGGCCAAGGCGCTGGAGCTGTTTCATGCGAGTGGGAAATAGGTAGTT            360
 G  L  T  V  A  K  A  L  E  L  F  H  A  S  G  G  K  *
                      270                     280

TTGCAGGTATACCTGCATGGGTAAATGTAAAAGTCGAATAAAAAATGTCACAGAGTGACGG       420

ACTGATATAAATAAATTAATAAACATGTCATCATGAGTGACAGACTGATATAAATAAAATA₂₀     499
```

FIG. 3C

METHOD OF PRODUCING PATHOGEN-RESISTANT PLANTS

This application is a continuation of application Ser. No. 08/215,163, filed on Mar. 21, 1994, now abandoned, which is a continuation of U.S. Pat. No. 07/810,390, filed on Dec. 19, 1991, now abandoned.

The invention relates to a method of producing pathogen-resistant plants, plants and plant components produced by the method, new DNA transfer vectors and DNA expression vectors and finally the use of a protein-synthesis inhibitor protein for producing pharmaceutical preparations.

BACKGROUND OF THE INVENTION

It is known for example from Ann. Rev. Plant Physiol. 1979, 30:105–130 and Ann. Rev. Plant. Physiol. 1984, 35:34–275 that plants utilize a great variety of mechanisms to protect themselves from infections by pathogens. These mechanisms include for example modifications in the cell wall structure, synthesis of toxically acting phytoalexines, accumulation of so-called PR proteins (pathogenesis-related proteins), protease inhibitors and enzymes with hydrolytic functions.

It is further known for example from Biochem. J. 1983, 216:617–625 that various plants can generate proteins which have the ability of inhibiting the ribosomes of eucaryotes. Characteristic of such proteins inhibiting protein synthesis is the property of not influencing the plant-inherent ribosomes whilst they inactivate the plant-foreign ribosomes. Such proteins have become known in particular under the designation "RIP" proteins (ribosome-inhibiting proteins). Of most of these proteins, only their molecular weight and their mode of action are known.

Among the plants in which RIP proteins have been found are the barleys. Thus, in Carlsberg Res. Commun. Vol.51, 1986, p. 129–141, the purified protein, the molecular weight thereof and the amino acid sequence are described.

It is further known, for example from Biochemica et Biophysica Acta 880, 1986, p. 161–170 that RIP proteins are able to inhibit "in vitro" pathogens.

SUMMARY OF THE INVENTION

In the investigation of in particular barley plants the genes which encode for protein-synthesis inhibitors (PSI) have been identified. It has been found that these PSI genes encode for PSI proteins which can effectively block the protein synthesis of plant pathogens.

It has further been found that PSI genes isolated for example from barley plants can be fused with a great variety of active promotors, for example the wun1-promotor, which is described in detail in "The Plant Cell 1", 1989, p.151–158 and that such promotor gene fusions can be incorporated into the genotype of plants and can produce transgenic plants which exhibit newly acquired pathogenic resistance.

It has further been found that the PSI protein can also be employed for producing pharmaceutical preparations which can be used to treat humans and animals affected by fungal, bacterial, viral or other pathogenic agents.

The PSI protein can be made in large amounts by introducing the PSI gene into bacterial overproducers. Purified PSI protein may be introduced in the form of infusion solutions into the blood path of humans or animals. The PSI protein inhibits the pathogen (for example AIDS viruses) without damaging the organism. The pathogen specificity of the PSI protein can possibly be further increased by coupling the PSI protein to pathogen-specific antibodies.

It is also possible to treat degenerate cells (cancer) in humans or animals by employing PSI protein. Thus, purified PSI protein or PSI protein which has been coupled to antibodies which detect specifically degenerate cells can be introduced into the blood path for destroying degenerate cells. Other forms of administration are possible, for example in capsules.

Suitable infusion solutions can be prepared by methods as usual and known for the preparation of aqueous infusion solutions.

Accordingly, the subject of the invention is a method of producing pathogen-resistant plants as is characterized in the claims, new DNA transfer vectors and DNA expression vectors as well as plants and plant components which can be obtained by the method according to the invention.

The subject of the invention is furthermore the use of the protein-synthesis inhibitor protein obtained by introduction of the protein-synthesis inhibitor gene into bacterial overproducers for the production of pharmaceutical preparations for the generation of pathogenic resistances, combatting pathogenic affection and/or degenerate cells.

Typical plant pathogens of which the protein synthesis can be inhibited by incorporation of a PSI gene are for example the fungi *Trichoderma reesei* and *Fusarium sporotrichioides*. (Attention is drawn to the review in M. Klinkowski, E. Mühle, E. Reinmuth and H. Bochow: "Phytopathology and plant protection I+II", Akademie-Verlag, Berlin, 1974).

As is known, fusarium fungi attack mainly cereals and maize plants whilst fungi of the genus Trichoderma are to be found mainly on maize kernels.

It has surprisingly been found that the pathogen-inhibiting properties of PSI genes isolated for example from barley plants can also be transferred to plants of different species. Thus, it has been found for example that under the control of an active promotor, for example the wun1-promotor, a PSI gene isolated from barley can be incorporated into the genotype of tobacco plants. Tobacco plants which thereupon produce the PSI protein exhibit newly acquired resistance properties against for example the plant pathogenic *Rhizoctonia solani*. Rhizoctonia causes the so-called root-killer disease (affection of stem and root) in various plants, including potato and tobacco plants. Thus, newly acquired resistance properties in plants are directly correlated to the expression of PSI genes.

Apart from barley, protein-synthesis inhibitor genes can be isolated for example from all monocotyl and dicotyl plants and fused with a great variety of active promotors, for example pathogen-inducible promotors, constitutive promotors, development-specific promotors, organ-specific promotors and inducible promotors.

The following can be named as examples of plants into the genotype of which the new protein-synthesis inhibitor genes can be incorporated under the control of an active promotor:

all monocotyl useful plants, such as cereals all dicotyl useful plants, such as *solanaceae* and *cucurbitaceae*.

The method according to the invention is thus particularly suitable for producing pathogen-resistant plants. However, through the expression of the protein-synthesis-inhibitor gene a resistance to insects, fungi, bacteria, viruses and viroids can also be achieved in humans and animals.

According to an advantageous further development, for executing the method according to the invention a protein-synthesis inhibitor gene is suitable which has the DNA sequence illustrated in FIG. 3A. (SEQ. ID NO. 1) However, it will be apparent to the person skilled in the art that apart from this DNA sequence similar DNA sequences can be used to solve the problem set, for example a DNA sequence according to FIG. 3B (SEQ. ID NO. 2) which in the 5' region has been completed by a corresponding cDNA clone.

The invention will be explained in detail hereinafter by way of example with reference to the isolation of a PSI gene from barley, fusion of said gene with an active promotor and transfer of the fusion product into the genotype of tobacco plants.

BRIEF DESCRIPTION OF THE DRAWINGS

The Figures serve for a more detailed explanation of the invention. They show in detail.

The SDS-gel-electrophoretic separation is shown of protein fractions which have been formed in the purification of CHI protein (row 2–5), PSI protein (row 7–11) and BGL protein (row 13–17) from barley seeds. With the aid of specific antibodies the corresponding proteins can be detected. The abbreviations mean:

% $(NH_4)_2SO_4$: Proteins which have been precipitated by the salt.

% sup.: Proteins which have not been precipitated by the salt.

CM: Proteins which have not been bound by the CM column.

fra.: Protein fraction from CM column.

pur.: highly pure protein.

MW: Protein-size standard in kDalton.

FIG. 2:A–2B: Fungus growth test with purified protein

Spores of Trichoderma reesei (A) and Fusarium sporotrichioides (B) were grown in a total volume of 135 µl medium/well of a microtiter plate and mixed with 0.05–1.5 µg of the particular protein indicated. Each point marking is the result of 5 independent measurements with relative standard deviations of 3.6% for (A) and 7.3% for (B). 100% fungus growth leads to an $O.D._{540}$ of 0.40 (A) and 0.41 (B).

FIG. 3:A–3C: Nucleotide sequence of the isolated PSI-cDNA clones

FIG. 3A–3B: SEQ. ID NO. 1 The cDNA clone is 1078 nucleotides large. It includes a 42 bp large 5'-untranslated region, an open read frame of 843 bp (the stop codon is marked with *) and a 193 bp large 3'-untranslated end. Possible polyadenylation signals are underlined. The amino acid sequence resulting from the open read frame is indicated beneath the corresponding sequence.

FIG. 3C: SEQ. ID NO. 2 Nucleotide sequence of an incomplete PSI-cDNA clone. Possible polyadenylation signals are underlined.

Figure 4:
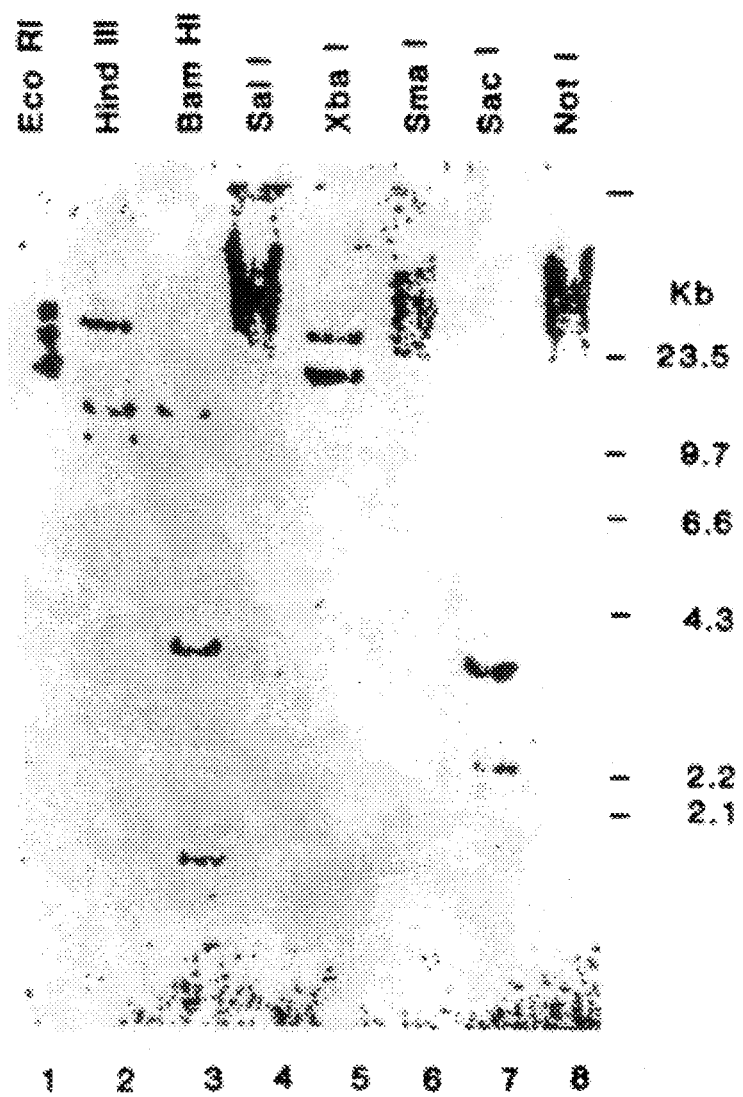

FIG. 4: Organization of PSI genes in the barley genome

DNA from barley embryos was cut with various restriction enzymes, gel-electrophoretically separated, transferred to nylon membranes and hybridized against radioactively marked PSI-cDNA. On the basis of the number of hybridizing bands conclusions can be drawn about the PSI copy number in the genome. The size standard is indicated in kilobase pairs (Kb).

Figure 5:
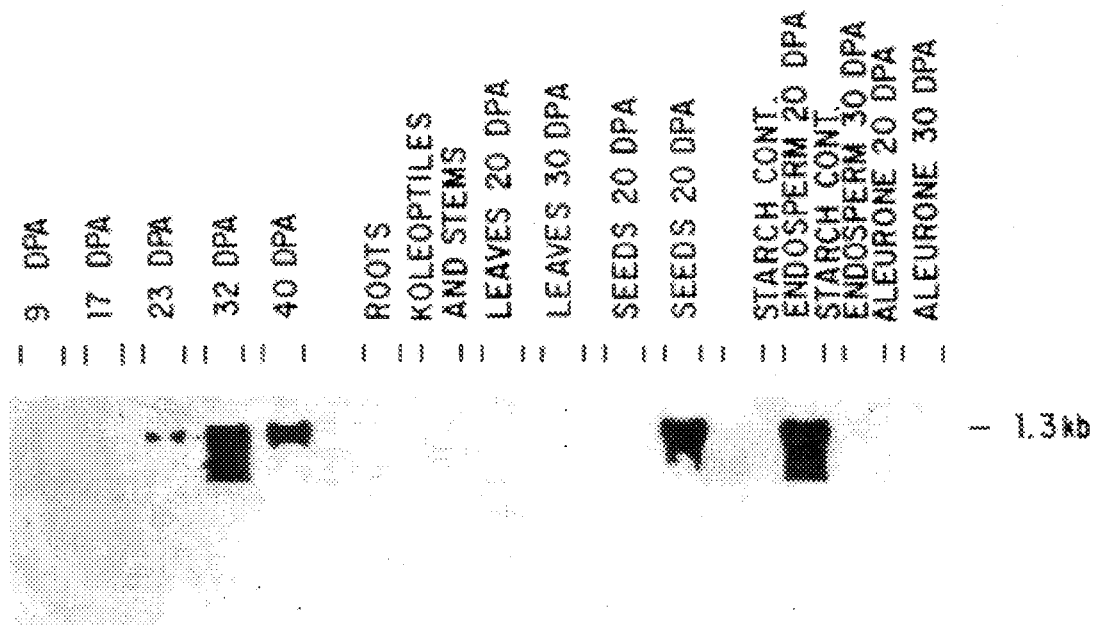

FIG. 5: Development-specific and organ-specific expression of PSI-RNA in barley

RNA was isolated from different organs of barley plants and at different development stages. The RNA was hybridized after gel-electrophoretic application via the "Northern Blot Method" with respect to radioactively marked PSI-cDNA. PSI-RNA is specifically detectable in the starch-containing endosperm during the subsequent seed development as 1.3 Kb large RNA. DPA stands for days after the anthesis.

Figure 6:
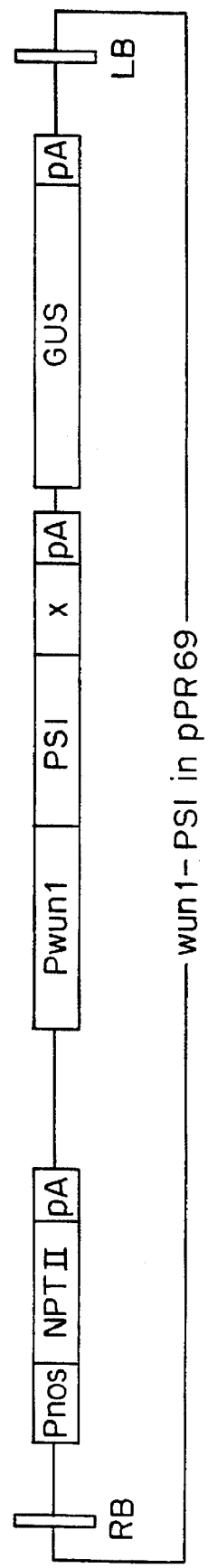

FIG. 6: Construction map of the chimeric gene wun1-PSI in pPR69

The wun1-promotor ("Pwun1"; about 1200 bp large) was fused transcriptionally with the PSI gene ("PSI"; about 1070 bp large). For RNA stability reasons, a residue of the CAT gene ("x"; about 500 bp large) and a polyadenylation signal ("pA"; about 200 bp large) were fused with the 3' of the PSI gene. This construct was cloned into the binary vector pPR69.

Figure 7:
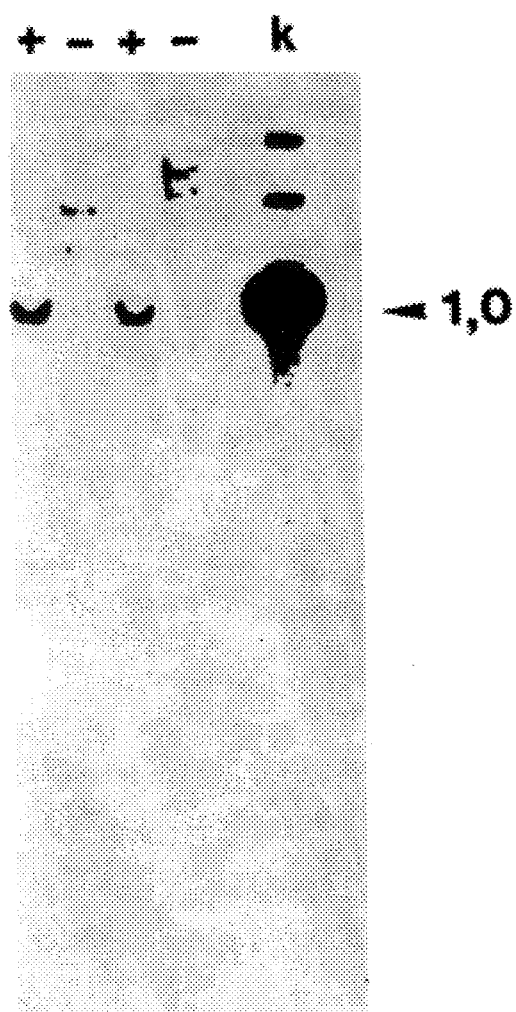

FIG. 7: Southern Blot Analysis of wun1-PSI-transgenic tobacco plants

To enable the correct integration of wun1-PSI-DNA into the tobacco genome to be analyzed, DNA was isolated from wun1-PSI-transgenic tobacco plants and cut with EcoRI. After the gel-electrophoretic separation of the DNA and the transfer of the DNA to nylon membranes hybridization was carried out with respect to radioactive PSI-cDNA. The plants designated with a (+) exhibit correct integration of the wun1-PSI-DNA. The size of the hybridizing bands is 1.07 Kb and is identical to the size of the plasmid-DNA of wun1-PSI in pPR69 (K) applied for control. Plants designated by (–) were discarded because of the presence of additional or incorrect large DNA bands.

Figure 8:
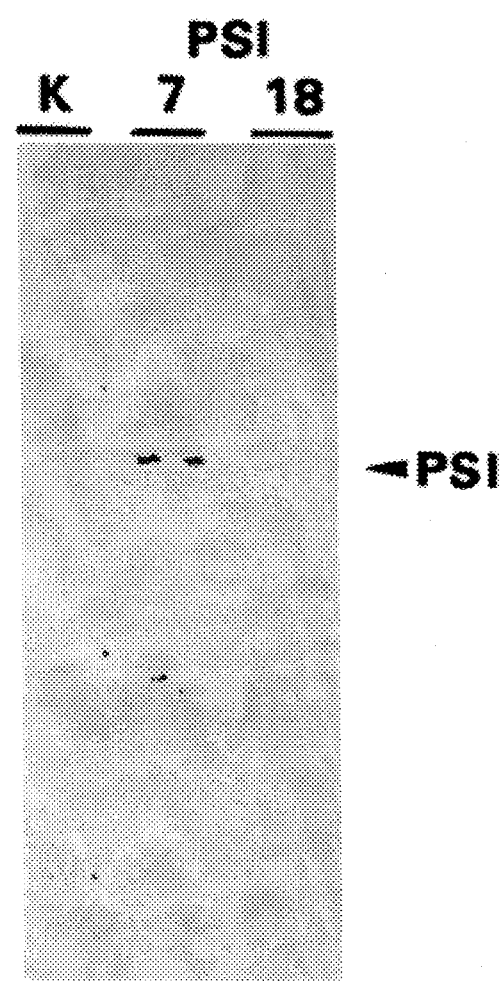

FIG. 8: Northern Blot Analysis of wun1-PSI-transgenic tobacco plants

100 µg leaf RNA from Rhizoctonia solani-infected tobacco plants were separated gel-electrophoretically, transferred to nylon membranes and hybridized with respect to radioactive PSI-cDNA. On the autoradiography, in the case of wun1-PSI-transgenic tobacco plants ("PSI-7; PSI-18) a PSI-RNA band can be seen. In untransformed tobacco plants (K) no PSI-RNA can be detected.

Figure 9:
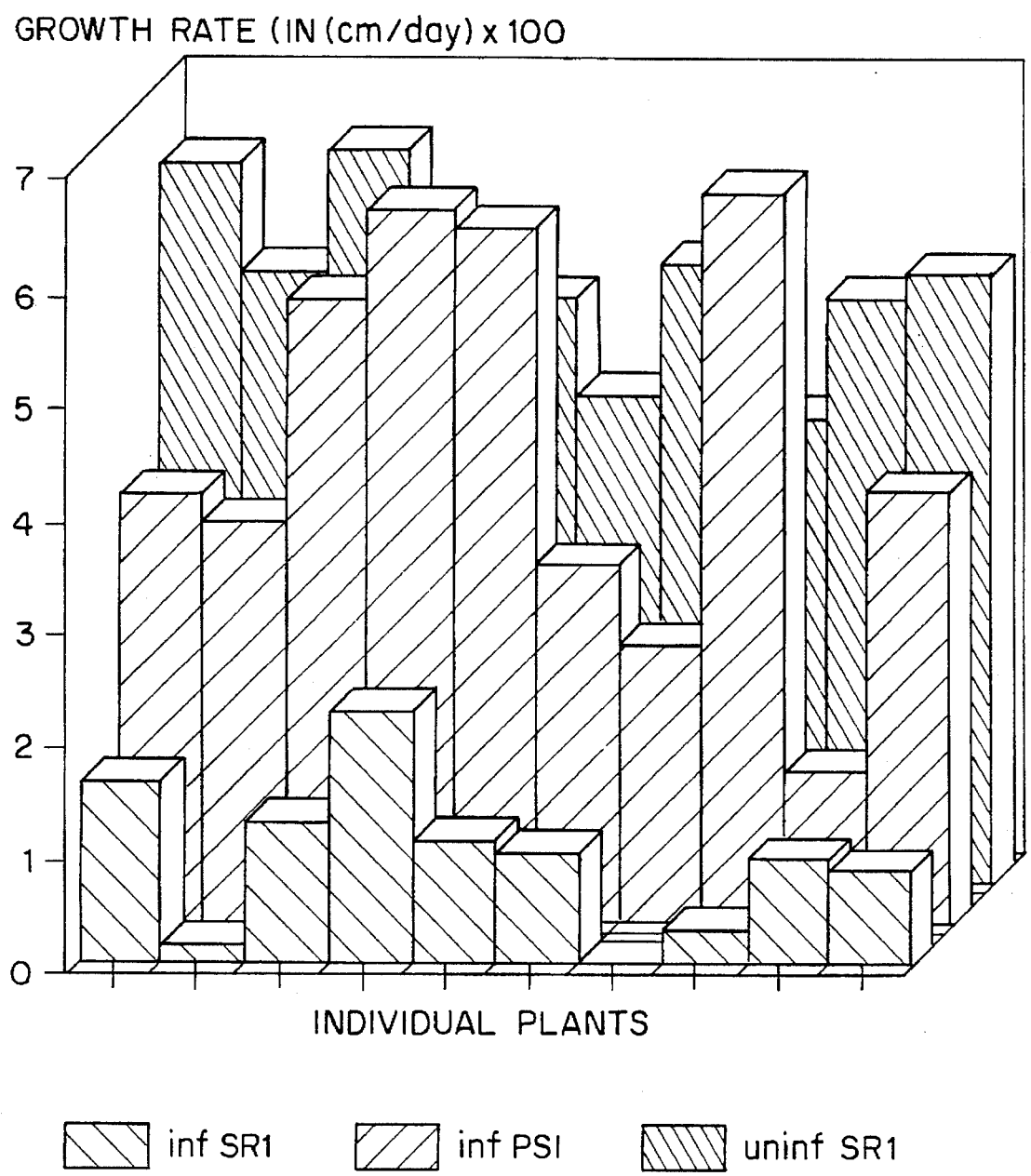

FIG. 9: Growth rates of individual tobacco plants infected with Rhizoctonia solani Each bar illustrated represents the growth of a tobacco plant over a period of about 10 days. From the slope of the growth curve, the 1n×100 was calculated so that the value obtained represents the growth rate. "inf. SRI": untransformed tobacco which was infected with Rhizoctonia solani. "inf.RIP: wun1-PSI-transgenic tobacco which was infected with Rhizoctonia solani. "uninf.SRI: untransformed tobacco which was not infected.

Figure 10:
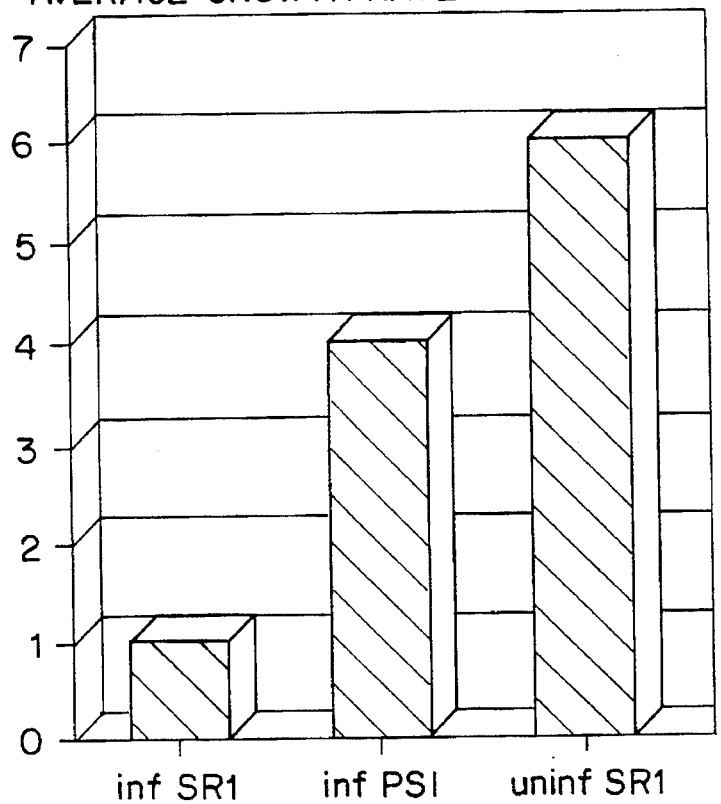

FIG. 10: Average growth rate with Rhizoctonia solani-infected tobacco plants

Illustration of the average growth rates which were calculated from the individual values shown in FIG. 9.

Figure 11:
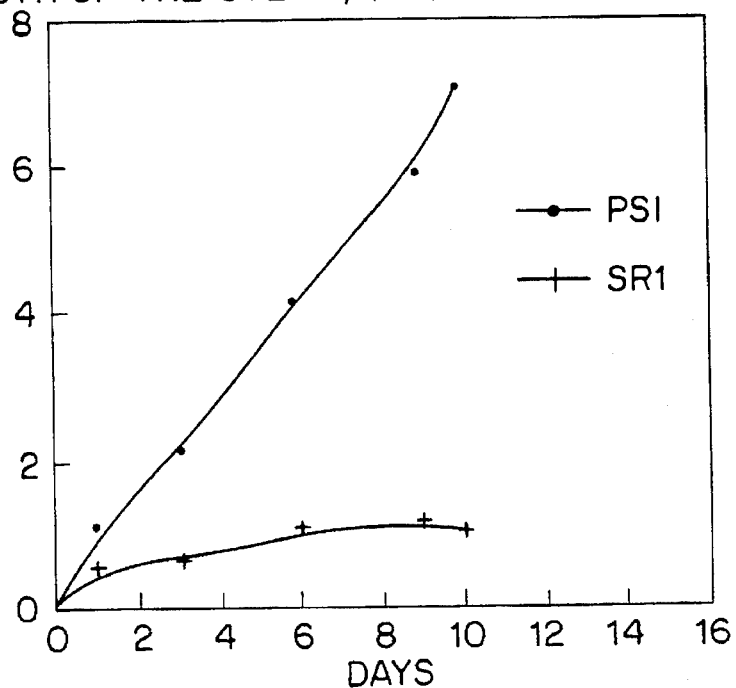

FIG. 11: Average stem growth of Rhizoctonia solani-infected tobacco plants

Average growth behaviour of 10 independent wun1-PSI-transgenic tobacco plants ("PSI") and 10 untransformed tobacco plants ("SRI") after infection with Rhizoctonia sulani. Along the abscissa the length of the stem is plotted (up to the vegetation point) and along the ordinate the number of days after the infection.

EXAMPLE 1

A. Materials Used

Media

For cultivating bacteria, media were used as described in detail by Maniatis, T. et al in "Molecular cloning: a laboratory manual" Cold Spring Harbour Laboratory, Cold Spring Harbour, N.Y. (1982).

Plant Media

The media used are derived from the media (MS) specified by Murashige, T. et al in "A rapid method for rapid growth and bioassays with tobacco tissue cultures"; Physiol. Plant., 15:473–497 (1962).

3MS: MS+3% saccharose

3MSC: MS+3% saccharose, 500 μg/ml claforan

3MC15: MS+2% saccharose, 500 μg/ml claforan, +100 μg/ml kanamycin sulfate

MSC16: MS+0.5 μg/ml BAP+0.1 μg/ml NAA+100 μg/ml kanamycin sulfate+500 μg/ml claforan For solid medium, 8 g/l bacto agar were additionally added.

Strains and Vectors

E. coli strains:

BMH 71-18: delta(lac-proAB), thi, supE; F'(laci$_L^C$, ZdeltaM15, proA$^+$B$^+$)

Attention is drawn to: Messing, J. et al. "Plant Gene Structure" in: Kosuge, F., Meredith, C.P., Hollaender, A. (Eds.). Genetic engineering of plants. Plenum Press, N.Y.: 211–227 (1983)

Agrobacteria strains: LBA 4404: (Hoekema et al., Nature 303:179–180 (1983)

Plasmids:

pUC8 (Vieira and Messing in "The puc plasmid, an M13mp7-derived system for insertion mutagenesis and sequencing with synthetic universal primers. Gene, 19:259–268 (1982).

pPR69 (a derivative of the bin 19, cf. "Bevan, M. Binary Agrobacterium vectors for plant transformation", Nucl. Acids, Res. 12:8711–8721 (1984)).

Plants:

*Hordeum vulgare* L. cv. Piggy

*Nicotiana tabacum* SRI

B. Applied Methods

Unless otherwise indicated, all the molecular biological standard methods were carried out as in Maniatis et al., (1982), such as for example restriction analysis, plasmid isolation, minipreparations of plasmid-DNA, transformation of bacteria, etc..

Plant Material

Ripe barley seeds (*Hordeum vulgare* L. cv. Piggy) were harvested at various times after the anthesis, frozen in liquid nitrogen and stored at −80° C.

Isolation and Purification of PSI, CHI and BGL Protein

PSI and CHI protein:

10 kg ripe barley seeds were worked to a fine flour (particle size: less than 0.5 mm in diameter). After addition of 100 liter extraction buffer (50 mM phosphate buffer, pH 6.5; 100 mM NaCl; 2.5 mM ascorbic acid; 2.5 mM EDTA; 3 mM beta-mercapto-EtOH) and stirring at 4° C. for 2 hours, the supernatant is filtered off. For this purpose, with the aid of an ultracentrifuge the volume of the supernatant is reduced to 6 liters (filters used: DDS membranes (ultrafiltration membranes of polysulphone) which retain all proteins smaller than 20 kDa). The supernatant is now precipitated with 40–70% $(NH_4)_2SO_4$. The pellet obtained is dissolved in 80 mM PMSF and dialyzed against 2 mM Na phosphate buffer, pH 6.5, to which 80 mM PMSF was added. The protein solution is now loaded via ion exchange chromatography on CM52 (Whatman) and eluted with 50 mM Na phosphate containing increasing NaCl concentrations (0.05 to 1.0M NaCl with more than 10 elution steps).

BGL protein:

Barley seeds were germinated for 12 days, lyophilized and treated with extraction buffer (see above) (1.6 kg seed/25 liter extraction buffer). After a 40% $(NH_4)_2SO_4$ precipitation the supernatant was dialyzed and purified over a CM52 and mono-S column. Isolated BGL protein was tested as regards purity by western blots and N-terminal sequencing.

Preparation of PSI Antibodies

Antibodies were prepared with respect to purified PSI-II protein in rabbits by conventional methods.

Fungus Growth Test with Purified Protein

*Trichoderma reesei* and *Fusarium sporotrichioides* (ATCC collection, Rockville) were grown on potato dextrose agar (Difco Co.) at 25° C. Spores of 8-day old cultures were harvested by the method of Broekaert, W.F. et al. "An automated quantitative assay for fungal growth inhibition" FEMS Microbiology Letters (1990) and stored at −20° C. in 20% glycerol. Within the scope of the fungus growth test a spore suspension (10000 spores/ml) was mixed with 100 μl potato dextrose solution and 35 μl of a protein fraction to be tested and incubated at 25° C. As described by Broekaert et al., the growth of the fungus is linearly correlated with the increase of the optical density at 540 nm. Protein fractions with fungus growth-inhibiting effect thus lead to a lower increase in the optical density than protein fractions with no effect.

Isolation of the PSI-cDNA Clones from Barley

From ripe barley seeds (*Hordeum vulgare* L cv. Piggy) polyA$^+$-RNA was isolated and deposited in a cDNA expression bank in lambda-gt-11 phages. Attention is drawn to Leah, R. and Mundy, J. "The biofunctional a-amylase/ subtilisin inhibitor of barley; nucleotide sequence and patterns of seed-specific expression". Plant Mol. Biol. 12:673–682 (1989). With the aid of monospecific antibodies PSI (cf. Mundy, J. et al "Differential synthesis in vitro of barley aleurone and starchy endosperm proteins." Plant Physiol. 81:630–636 (1986) PSI-containing cDNA clones were identified.

Analysis of the PSI Nucleotide Sequence

PSI-positive lambda-gh11-phages were isolated, subcloned and sequenced by the didoxy sequencing method of Sanger et al., "DNA sequencing with chain-terminating inhibitors." Proc. Natl. Acad. Sci USA, 74:5463–5467 (1977).

DNA Transfer in Agrobacteria

Transformation:

The DNA cloned in *E. coli* was transferred by the method described by Van Haute et al. in the work "Intergenic transfer and exchange recombination of restriction fragments cloned in pBR322: a novel strategy for reversed genetics of Ti-plasmids of Agrobacterium tumefaciens", EMBO J., 2:411–418 (1983), by conjugation to A. tumefaciens LBA4404 (cf. Hoekema et al. "A binary plant vector strategy based on separation of vir- and T-region of A-tumefaciens", Nature 303:179–180 (1983)).

DNA Analysis

Checking of the DNA transfer to the agrobacterium was effected by isolation of the agrobacteria DNA by the method described by Ebert et al. in "Identification of an essential upstream element in the nopalin synthase promotor by stable and transient assays." Proc. Natl. Acad. Sci USA 84:5745–5749 (1987). Restriction cleavage of the DNA, transfer to nitrocellulose and hybridization with respect to the corresponding radioactive probe providing information on a successful DNA transfer to agrobacterium.

Transformation of Tobacco Plants with Agrobacteria

Growth of agrobacteria:

The agrobacteria LBA4404 necessary for the infection were grown in selective antibiotica medium (cf. Zambrisky et al. "Ti-Plasmid vector for the introduction of DNA into plant cells without alteration of their normal capacity". EMBO J., 1:147–152 (1983)), sedimented by centrifugation and washed in YEB medium without antibiotica (YEB=0.5 meat extract; 0.2% yeast extract; 0.5% peptone; 0.5% saccharose; 2 mM $MgSO_4$). After again sedimenting and taking up in 3 MS medium, the bacteria could be used for the infection.

Leaf-slice infection:

For the leaf slice infection sterile leaves of the tobacco lines SRI were employed. Leaf fragments of about 1 cm in size were dipped into the agrobacteria suspension described above and subsequently transferred to 3MS medium. After incubation for 2 days with 16 hours light and at 25° C.–27° C., the leaf fragments were transferred to MSC16 medium. Shoots appearing after 4–6 weeks were cut off and placed on MSC15 medium. Shoots with root formation were further analyzed.

DNA analysis of plants:

The plant material is pounded with liquid nitrogen, mixed with 10 volumes extraction buffer (10 mM tris-HCl (pH 8); 100 mM NaCl, 1 mM EDTA, proteinase K; pancreatic Rnase) and incubated, extracted with phenol and the supernatant precipitated with EtOH. The restriction digestion of the isolated DNA, the gel-electrophoretic separation of the DNA with Agarose and the transfer of the DNA to a nylon membrane is described in Maniatis et al. (1982). The hybridizing with respect to radioactively marked DNA specimens was carried out by a method described by Logemann et al. in the work "Improved method for the isolation of RNA from plant tissues", Anal. Biochem., 163:16–20 (1987).

RNA Analysis of Plants

Barley plants:

The isolation of total RNA and polyA⁺RNA was carried out in accordance with Leah and Mundy et al. (1989). The gel-electrophoretic separation with formaldehyde gels, the transfer to nylon membranes and the hybridizing with respect to radioactively marked DNA specimens was carried out according to Maniatis et al. (1982).

Transgenic tobacco and potato plants:

The isolation of total RNA from various organs, the transfer to nylon membranes and the hybridizing with respect to radioactively marked DNA specimens was carried out according to Logemann et al. (1987).

Protein Analysis of Transgenic Plants

Lyophilized leaf material was pounded in the extraction buffer (10 mM tris pH 8.0; 1 mM EDTA; 100 mM NaCl; 2% SDS) and the protein concentration adjusted to 1 mg/ml. The gel-electrophoretic separation of the protein was carried out with the Phast-gel-system (Pharmacia), 1 μg protein per slot being applied. The separated proteins were transferred to nitrocellulose (diffusion blots by 20-minute application of the nitrocellulose to the protein gel at 70° C.) and analyzing by employing specific antibodies (western blot analysis according to the protoblot system of the Promega company).

Infection of Transgenic Plants with *Rhizoctonia solani*

The fungus *Rhizoctonia solani* is grown in a liquid medium (potato dextrose agar of the Difco company) at 28° C. and harvested after 5–6 days. By means of a Büchner funnel and connected suction bottle the medium is extracted. The remaining fungus mycel is cut into fragments as small as possible with a scalpel. The desired amount of fungus mycel is weighed in and thoroughly mixed with 5 liters of sterile standard soil. This soil was spread in a dish and the plants to be tested planted therein. The growth of the plants is determined every 24 hours by determining the shoot length (ground-vegetation point distance).

Results

Figure 1:
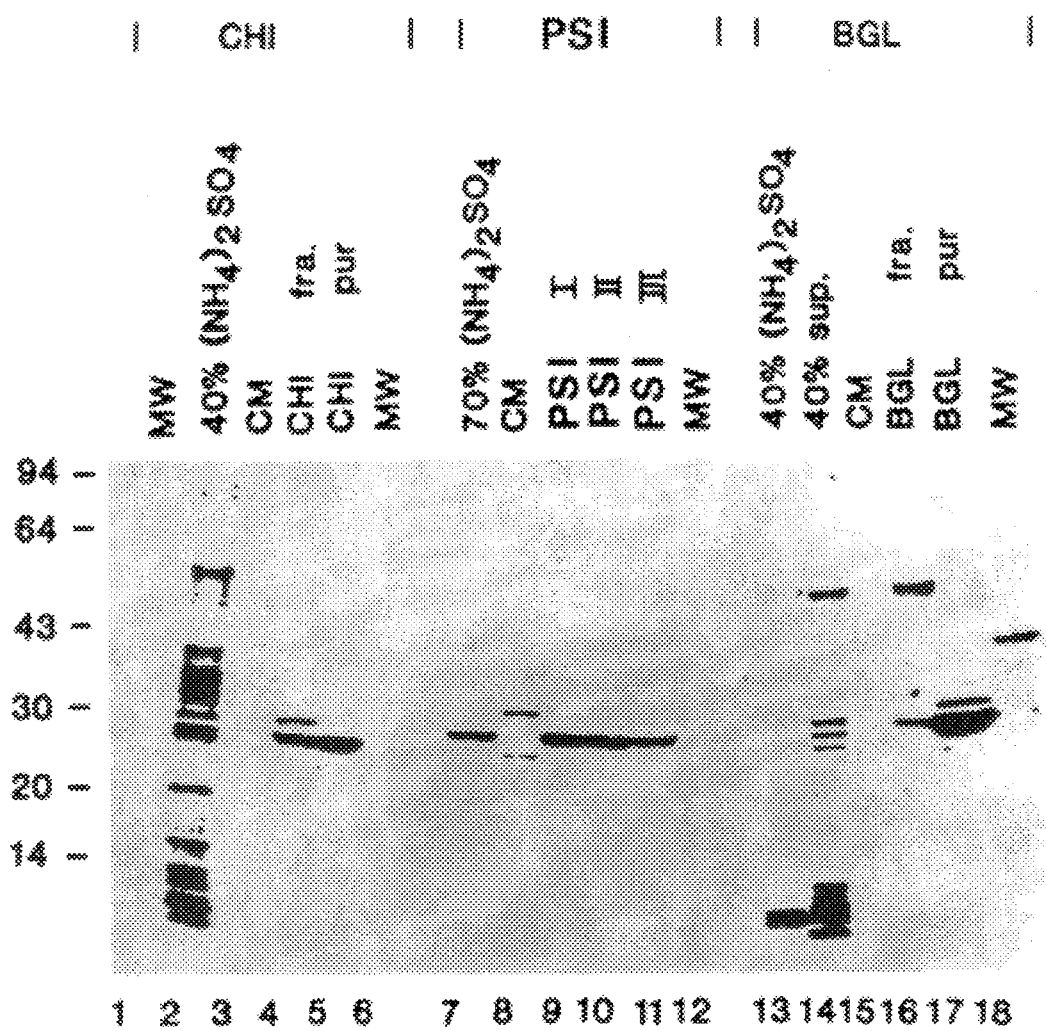
FIG. 1: Purification of CHI, BGL and PSI proteins from barley

Isolation and purification of PSI, CHI and BGL proteins from barley seeds:

The isolation of CHI and PSI protein from ripe barley seeds (*Hordeum vulgate L. cv.* Piggy) is described in "Methods". The protein fractions forming within the scope of the various purifying steps were applied to a denaturating acrylic amide gel and CHI or PSI proteins represented by silver-marked CHI or PSI antibodies (FIG. 1). CHI or PSI protein can be detected after 40% and 70% $(NH_4)_2SO_4$ precipitation (row 2, 7) after subsequent separation via Whatman CM52 (row 3, 4, 8) and after the following purification via a mono-S-column (row 5, 9, 10, 11). Rows 9, 10 and 11 of FIG. 1 show that three different PSI isoforms (PSI I, II, III) have been isolated which distinguish themselves by their different running behaviour in the CM52 column.

The specific activity of purified CHI protein was determined in accordance with Molano et al., "A rapid and sensitive assay for chitinase using tritiated chitin", Anal. Biochem. 88:648–656 (1977) and is 22 mg diacetyl chitobiose/minute/mg protein.

The purified PSI protein exhibits the following activity:

3–30 ng PSI are able to inhibit 50% of the RNA translation in reticulocyte lysates.

BGL protein was purified from 12-day old barley seedlings by $(NH_4)_2SO_4$ precipitation, separation via CM52 and a mono-S column (see "Methods") and detected with the aid of BGL antibodies (FIG. 1, rows 13–17). The specific activity of purified BGL protein is 25 mg glucose-equivalent/minute/mg enzyme.

Fungus growth test with purified proteins:

As described in "Methods", various geni of fungus are grown each on 135 μl fungus medium in microtiter plates (96 wells/plate) and their growth followed photometrically. By adding various proteins the influence of the latter on the fungus growth can be analyzed.

Figure 2A:
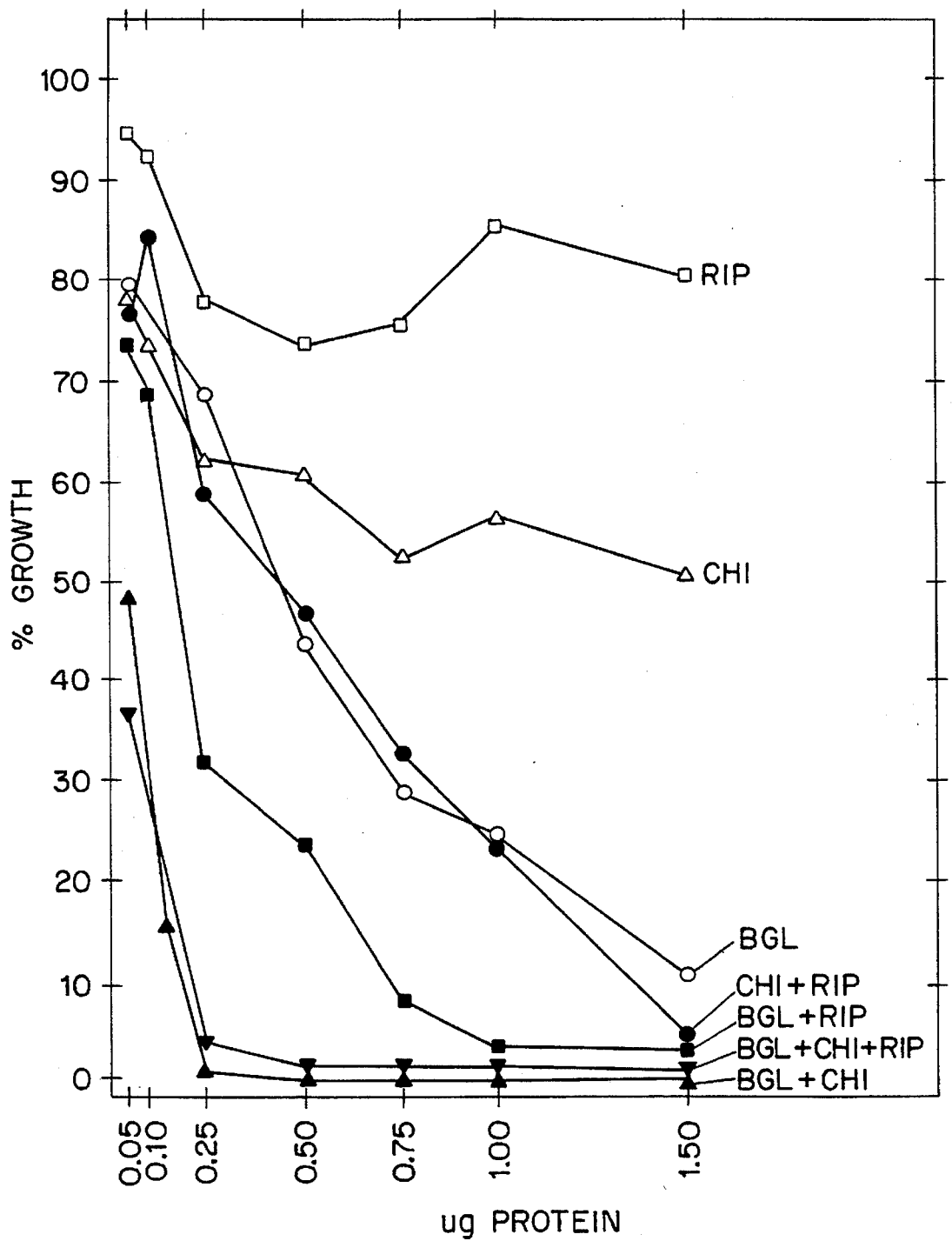

In FIG. 2A the growth behaviour of the fungus *trichoderma reesei* is illustrated. The use of 1.5 µg PSI/well inhibits the fungus growth by only 20%. In contrast, the growth is inhibited by more than 95% if 0.25 µg of each of the proteins PSI, CHI and BGL are combined with each other. A 95% inhibition is also obtained by the combination PSI/BGL (in each case 1.0 µg protein) or by the combination PSI/CHI (in each case 1.5 µg protein).

Figure 2B:
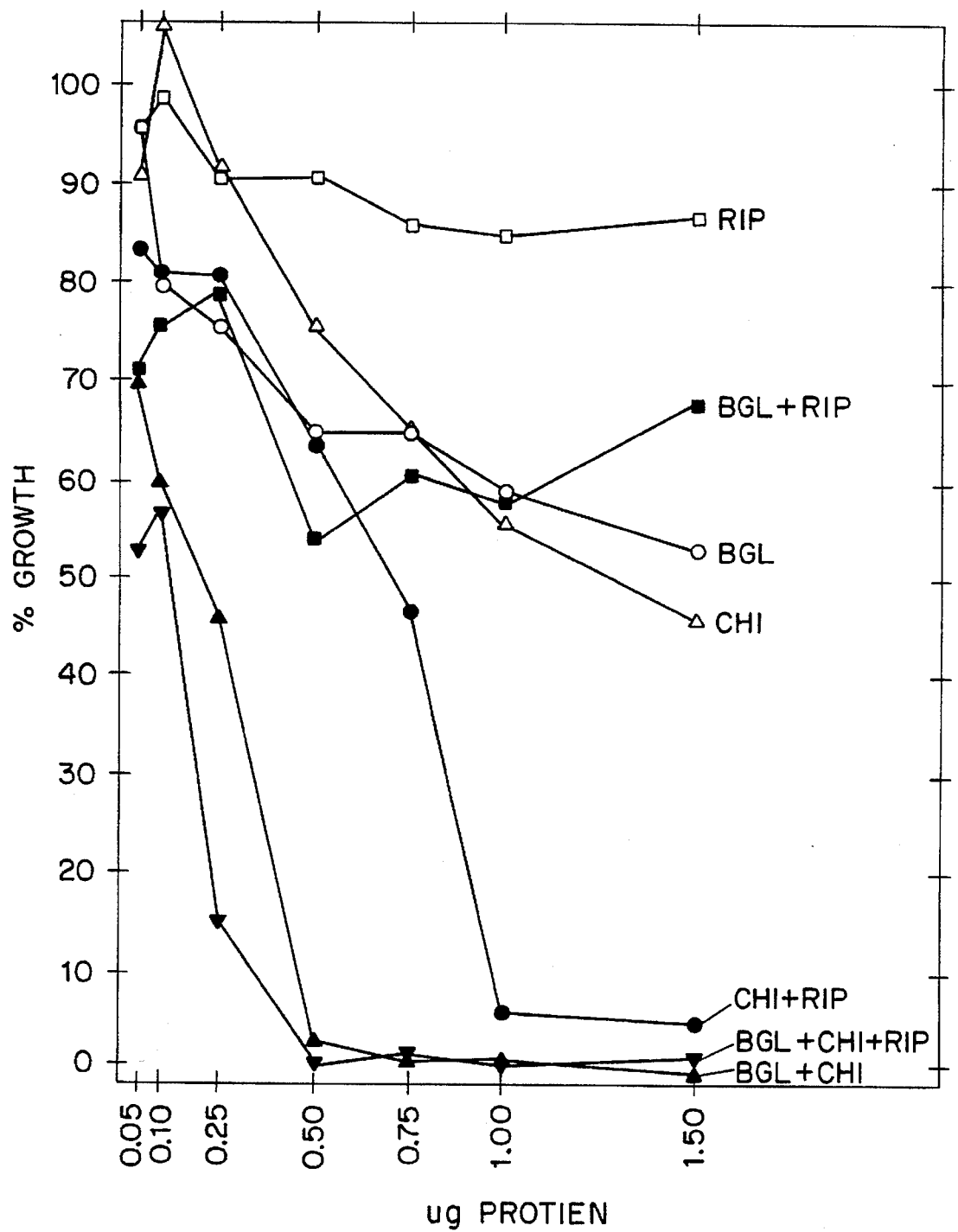

The growth of *Fusarium sporotrichioides* is also inhibited to 95% if 0.25 µg protein of each of PSI, CHI and BGL is combined (FIG. 2B). The combination PSI/CHI (in each case 1.0 μg protein) inhibits the fungus to the same extent. The use of 1.5 μg PSI or CHI or BGL alone however leads to significantly lower inhibitions. A lower effect is also obtained with the combination PSI/BGL.

The data determined in FIGS. 2A and 2B show that the use of PSI alone has a relatively low inhibition effect against the fungi used here. The combination with the chitinase CHI (FIG. 2A, B) or with the glucanase BGL (FIG. 2A) however considerably enhances the inhibition effect.

Isolation and sequencing of a PSI-cDNA clone:

From ripe barley seeds of the type *Hordeum vulgare L. cv.* Piggy poly$A^+$RNA was isolated, transformed to cDNA and cloned in lambda-gt-11 phages (see "Material and Methods"). An almost complete PSI-cDNA clone could be identified by using PSI antibodies. Sequencing of the PSI-cDNA clone gave the following data (FIG. 3A–3B):

The PSI clone has a length of 1087 bp.

The GC-rich open read frame encodes for a protein with a molecular weight of 29,976 Dalton.

The PSI protein does not contain any signal peptide.

The PSI protein starts with the amino acid methionine and thus conforms with the protein start of the naturally occurring PSI protein. It is therefore to be expected that the PSI protein is a cytosolic protein.

The DNA sequence shown in FIG. 3C is incomplete but does exhibit substantial homologies to the cDNA clone according to FIG. 3A–3B and is suitable for solving the problem set if the DNA sequence shown in the 5' region is completed by a corresponding cDNA clone.

Detection of PSI genes in the barley genome:

The use of the PSI-cDNA clone as radioactive probe permits an analysis of the barley genome with regard to the organization and number of PSI genes. DNA was isolated from barley embryos, cut with various restriction enzymes and hybridized with respect to the PSI-cDNA specimen. As shown in FIG. 4, principally three fragments hybridize with respect to PSI; therefore, three PSI genes per haploid genome are to be expected.

Detection of PSI-mRNA in barley seeds:

The expression of PSI-mRNA in various organs of barley seeds and within the scope of the seed development was determined with the aid of northern blot analyses (see "Material and Methods"). As FIG. 5 shows, no PSI-mRNA is present in barley roots, stems and leaves or in the aleurone layer of barley seeds. In contrast, large amounts of PSI-mRNA are found in the starch-containing endosperm from seeds provided that the seeds are in a late development stage. No PSI-mRNA is present in young endosperm.

Fusion of a PSI gene with the wun1 promotor and transfer to tobacco plants:

As described in FIG. 6, the PSI-cDNA clone is transcriptionally fused with the wund and pathogen-inducible promotor wun1.

The wun1-promoter (1022 bp) and 179 bp of the 5'-untranslated region of wun1 is fused with the PSI-cDNA clone isolated via EcoRI from the cDNA bank. The PSI gene has its own polyadenylation signal, the functionality of which in dicotyl plants can however so far only be presumed. Two additional elements were cloned behind the PSI gene to increase the stability of the PSI-mRNA. An approximately 500 bp long subsequence of the CAT gene (CAT-chloro-amphenicolacetyl transferase) was fused at 3' of the PSI gene. At 3' of the CAT subsequence the polyadenylation signal of the 35S gene of the cauliflower mosaic virus was used as terminating signal, the functionality of which in dicotyl plants is known.

The chimeric gene wun1-PSI was cloned via the HindIII cutting points into the binary vector pPR69, the designation of which is now "wun1-PSI in pPR69". Wun1-PSI in pPR69 was transformed by means of the agrobacterium tumefaciens transformation system in tobacco plants and kanamycin-resistant tobacco plants regenerated.

Detection of the wun1-PSI gene in transgenic plants:

With the aid of the southern blot analysis the wun1-PSI transgenic tobacco plants were investigated with regard to the correct integration of wun1-PSI into the tobacco genome. As FIG. 7 shows, the size of the hybridizing DNA bands from the transgenic tobacco plants corresponds to the size of the fragment introduced. Correct integration of wun1-PSI into the tobacco genome is therefore probable.

Determinations of PSI gene expressions in transgenic tobacco plants:

50 μg total RNA was isolated from fungal infected wun1-PSI transgenic tobacco leaves and investigated for the presence of PSI-mRNA (FIG. 8). No PSI-mRNA was detected in untransformed tobacco plants, irrespective of whether the leaves were in tact, injured or fungally infected. In tobacco leaves of fungally infected transgenic plants an RNA band hybridizing with PSI is apparent. The detection of PSI proteins in transgenic tobacco plants was carried out by the western blot method.

Infection of wun1-PSI-transgenic tobacco plants with *Rhizoctonia solani:*

Various independent wun1-PSI-transgenic plants were placed as approximately 10 cm sized plants in soil which had been infected with *Rhizoctonia solani* (5 g/5 liters soil). By daily measuring the plant size (plant vegetation point –soil distance) the growth of the plants was recorded for the next approximately two weeks. The control plants used were untransformed tobacco plants which 1. were likewise planted in soil infected with *Rhizoctonia solani* (5g/5 liters soil);

2. were planted in soil without addition of *Rhizoctonia solani.*

FIG. 9 shows the growth behaviour of the individual plants under the corresponding conditions. The growth rate of untransformed tobacco plants is very low in *Rhizoctonia solani*-containing soil. In contrast, Wun1-PSI-transgenic tobacco plants exhibit a substantially higher growth rate on soil containing *Rhizoctonia solani.*

The growth rate is only slightly less than the rate of untransformed tobacco plants which had been grown in fungus-free soil.

FIG. 10 describes the statistical mean value from the individual values shown in FIG. 9.

FIG. 11. shows the average growth of tobacco plants under various conditions. In a period of about 10 days untransformed tobacco plants grow about 1 cm on *Rhizoctonia solani*-containing soil. Wun1-PSI-transgenic tobacco plants grow about 4 cm/10 days on *Rhizoctonia solani*- containing soil. Untransformed tobacco plants kept on Rhizoctonia solani-free soil grow about 6 cm in about 10 days.

EXAMPLE 2

Isolation and Purification of the PSI Protein from Bacterial Overproducers

An example of a suitable plasmid for bacterial overproduction of PSI proteins is the plasmid pKK223-3 (Manufacturer: Pharmazia).

An IPTG (isopropyl-β-D-thiogalactoside) inducible tac-promotor permits for example the production of PSI protein. Various restriction points immediately behind the tac-promotor permit transcriptional fusion of the PSI gene with the tac-promotor. A strong ribosomal terminator (rrn) effects a defined stoppage of the transcription.

The PSI gene was cloned via the EcoRI cutting point in 5'3'-orientation into the EcoRI cutting point of pKK233-3 and transformed to JM105 bacteria. These bacteria were grown in 100 ml LB medium (50 mg/ml ampecilline) at 37° C. with vigorous shaking up to an $O.D._{550}=0.4$ and thereafter mixed with IPTG (2.5 mM final concentration). A further incubation for 4 hours at 37° C. followed. Thereafter, the 100 ml bacteria culture was centrifuged off for 15 minutes at 2500 rpm (Christ centrifuge, 4° C.) and the bacteria pellet taken up in 50 mM tris pH 8.0. The suspension was sonified with ultrasonic sound (several times for 2 minutes with 60% pulses) until the viscosity dropped appreciably.

Analogously to the description in "Methods" for "isolation and purifying of PSI protein" the PSI protein was then precipitated with 40–70% $(NH_4)_2SO_4$ and purified by ion exchange chromatography, for example CM52.

The purified and sterile-filtered protein was suitable for preparation of infusion solutions for therapeutical uses in humans and animals.

---

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 1032bp
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: no ( i v ) ANTI-SENSE: no ( v i ) ORIGINAL SOURCE:
        ( A ) ORGANISM: Hordeum vulgare L. cv.
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( x i ) SEQUENCE DESCRIPTION: SEQ ID NO: 1:

```
CTTAATAGCA  CATCTTGTCC  GTCTTAGCTT  TGCATTACAT  CC  ATG  GCG  GCA  AAG  ATG  GCG   60
                                                    Met  Ala  Ala  Lys  Met  Ala
                                                    -1    1                      5

AAG  AAC  GTG  GAC  AAG  CCG  CTC  TTC  ACC  GCG  ACG  TTC  AAC  GTC  CAG  GCC   108
Lys  Asn  Val  Asp  Lys  Pro  Leu  Phe  Thr  Ala  Thr  Phe  Asn  Val  Gln  Ala
               10                             15                       20

AGC  TCC  GCC  GAC  TAC  GCC  ACC  TTC  ATC  GCC  GGC  ATC  CGC  AAC  AAG  CTC   156
Ser  Ser  Ala  Asp  Tyr  Ala  Thr  Phe  Ile  Ala  Gly  Ile  Arg  Asn  Lys  Leu
                    25                        30                  35

CGC  AAC  CCG  GCG  CAC  TTC  TCC  CAC  AAC  CGC  CCC  GTG  CTG  CCG  CCG  GTC   204
Arg  Asn  Pro  Ala  His  Phe  Ser  His  Asn  Arg  Pro  Val  Leu  Pro  Pro  Val
                              45                                  50

GAG  CCC  AAC  GTC  CCG  CCG  AGC  AGG  TGG  TTC  CAC  GTC  GTG  CTC  AAG  GCC   252
Glu  Pro  Asn  Val  Pro  Pro  Ser  Arg  Trp  Phe  His  Val  Val  Leu  Lys  Ala
     55                       60                             65
```

```
TCG CCG ACC AGC GCC GGG CTC ACG CTG GCC ATT CGG GCG GAC AAC ATC        300
Ser Pro Thr Ser Ala Gly Leu Thr Leu Ala Ile Arg Ala Asp Asn Ile
70              75                  80                  85

TAC CTG GAG GGC TTC AAG AGC AGC GAC GGC ACC TGG TGG GAG CTC ACC        348
Tyr Leu Glu Gly Phe Lys Ser Ser Asp Gly Thr Trp Trp Glu Leu Thr
                90                  95                 100

CCG GGC CTC ATC CCC GGC GCC ACC TAC GTC GGG TTC GGC GGC ACC TAC        396
Pro Gly Leu Ile Pro Gly Ala Thr Tyr Val Gly Phe Gly Gly Thr Tyr
            105                 110                 115

CGC GAC CTC CTC GGC GAC ACC GAC AAG CTG ACC AAC GTC GCT CTC GGC        444
Arg Asp Leu Leu Gly Asp Thr Asp Lys Leu Thr Asn Val Ala Leu Gly
        120                 125                 130

CGG CAG CAG CTG GCG GAC GCG GTG ACC GCC CTC CAC GGG CGC ACC AAG        492
Arg Gln Gln Leu Ala Asp Ala Val Thr Ala Leu His Gly Arg Thr Lys
    135                 140                 145

GCC GAC AAG CCG TCC GGC CCG AAG CAG CAG CAG GCG AGG GAG GCG GTG        540
Ala Asp Lys Pro Ser Gly Pro Lys Gln Gln Gln Ala Arg Glu Ala Val
150                 155                 160                 165

ACG ACG CTG CTC CTC ATG GTG AAC GAG GCC ACG CGG TTC CAG ACG GTG        588
Thr Thr Leu Leu Leu Met Val Asn Glu Ala Thr Arg Phe Gln Thr Val
                170                 175                 180

TCT GGG TTC GTG GCC GGG TTG CTG CAC CCC AAG GCG GTG GAG AAG AAG        636
Ser Gly Phe Val Ala Gly Leu Leu His Pro Lys Ala Val Glu Lys Lys
            185                 190                 195

AGC GGG AAG ATC GGC AAT GAG ATG AAG GCC CAG GTG AAC GGG TGG CAG        684
Ser Gly Lys Ile Gly Asn Glu Met Lys Ala Gln Val Asn Gly Trp Gln
        200                 205                 210

GAC CTG TCC GCG GCG CTG CTG AAG ACG GAC GTG AAG CCT CCG CCG GGA        732
Asp Leu Ser Ala Ala Leu Leu Lys Thr Asp Val Lys Pro Pro Pro Gly
    215                 220                 225

AAG TCG CCA GCG AAG TTC GCG CCG ATC GAG AAG ATG GGC GTG AGG ACG        780
Lys Ser Pro Ala Lys Phe Ala Pro Ile Glu Lys Met Gly Val Arg Thr
230                 235                 240                 245

GCT GTA CAG GCC GCC AAC ACG CTG GGG ATC CTG CTG TTC GTG GAG GTG        828
Ala Val Gln Ala Ala Asn Thr Leu Gly Ile Leu Leu Phe Val Glu Val
                250                 255                 260

CCG GGT GGG TTG ACG GTG GCC AAG GCG CTG GAG CTG TTC CAT GCG AGT        876
Pro Gly Gly Leu Thr Val Ala Lys Ala Leu Glu Leu Phe His Ala Ser
            265                 270                 275

GGT GGG AAA TAGGTAGTTT TCCAGGTATA CCTGCATGGG TAGTGTAAAA GTCGAATAAA    935
Gly Gly Lys
        280

CATGTCACAG AGTGACGGAC TGATATAAAT AAATAAATAA ACGTGTCACA GAGTTACATA     995

TAAACAAATA AATAAATAAT TAAAAATGTC CAGTTTA                             1032
```

( 2 ) INFORMATION FOR SEQ ID NO: 2:

( i ) SEQUENCE CHARACTERISTICS:
        ( A ) LENGTH: 480bp
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: no ( i v ) ANTI-SENSE: no ( v i ) ORIGINAL SOURCE:
        ( A ) ORGANISM: Hordeum vulgare L. cv.
        ( B ) STRAIN:
        ( C ) INDIVIDUAL ISOLATE:

(D) DEVELOPMENTAL STAGE:
(E) HAPLOTYPE:
(F) TISSUE TYPE:
(G) CELL TYPE:
(H) CELL LINE:
(I) ORGANELLE:

(xi) SEQUENCE DESCRIPTION: SEQ ID NO: 2:

| GCG | GTG | ACG | ACG | CTG | CTC | CTC | ATG | GTG | AAC | GAG | GCC | ACG | CGG | TTC | CAG | 48 |
| Ala | Val | Thr | Thr | Leu | Leu | Leu | Met | Val | Asn | Glu | Ala | Thr | Arg | Phe | Gln | |
| 1 | | | | 5 | | | | | 10 | | | | | 15 | | |

| ACG | GTG | TCG | GGG | TTC | GTG | GCC | GGG | CTG | CTG | CAC | CCC | AAG | GCG | GTG | GAG | 96 |
| Thr | Val | Ser | Gly | Phe | Val | Ala | Gly | Leu | Leu | His | Pro | Lys | Ala | Val | Glu | |
| | | | 20 | | | | | | 25 | | | | | 30 | | |

| AAG | AAG | AGC | GGG | AAG | ATC | GGC | AAT | GAG | ATG | AAG | GCC | CAG | GTG | AAC | GGG | 144 |
| Lys | Lys | Ser | Gly | Lys | Ile | Gly | Asn | Glu | Met | Lys | Ala | Gln | Val | Asn | Gly | |
| | | 35 | | | | | 40 | | | | | 45 | | | | |

| TGG | CAG | GAC | CTG | TCC | GCG | GCG | CTG | CTG | AAG | ACG | GAC | GTG | AAG | CCC | CCG | 192 |
| Trp | Gln | Asp | Leu | Ser | Ala | Ala | Leu | Leu | Lys | Thr | Asp | Val | Lys | Pro | Pro | |
| | 50 | | | | | 55 | | | | | 60 | | | | | |

| CCG | GGA | AAG | TCG | CCA | GCG | AAG | TTC | ACG | CCG | ATC | GAG | AAG | ATG | GGC | GTG | 240 |
| Pro | Gly | Lys | Ser | Pro | Ala | Lys | Phe | Thr | Pro | Ile | Glu | Lys | Met | Gly | Val | |
| 65 | | | | | 70 | | | | | 75 | | | | | 80 | |

| AGG | ACT | GCT | GAG | CAG | GCT | GCG | GCT | ACT | TTG | GGG | ATC | CTG | CTG | TTC | GTT | 288 |
| Arg | Thr | Ala | Glu | Gln | Ala | Ala | Ala | Thr | Leu | Gly | Ile | Leu | Leu | Phe | Val | |
| | | | | 85 | | | | | 90 | | | | | 95 | | |

| GAG | GTG | CCG | GGT | GGG | TTG | ACG | GTG | GCC | AAG | GCG | CTG | GAG | CTG | TTT | CAT | 336 |
| Glu | Val | Pro | Gly | Gly | Leu | Thr | Val | Ala | Lys | Ala | Leu | Glu | Leu | Phe | His | |
| | | | 100 | | | | | 105 | | | | | 110 | | | |

| GCG | AGT | GGT | GGG | AAA | TAGGTAGTTT | TGCAGGTATA | CCTGCATGGG | TAAATGTAAA | 391 |
| Ala | Ser | Gly | Gly | Lys | | | | | |

AGTCGAATAA AAATGTCACA GAGTGACGGA CTGATATAAA TAAATTAATA AACATGTCAT 451

CATGAGTGAC AGACTGATAT AAATAAATA 480

We claim:

1. A method of producing fungus-resistant plants comprising introducing a protein-synthesis inhibitor gene or a fusion product of the protein-synthesis inhibitor gene into the genotype of plants under the control of an active promoter, wherein the protein-synthesis inhibitor gene comprises the following DNA sequence:

| SEQUENCE DESCRIPTION: SEQ ID NO. 1 | | | | | | | |
|---|---|---|---|---|---|---|---|
| CC | CTTAATAGCA GTCTTAGCTT | | | CATCTTGTCC TGCATTACAT | | | |
| | ATG Met −1 | GCG Ala 1 | GCA Ala | AAG Lys | ATG Met | GCG Ala 5 | 60 |
| AAG Lys | AAC Asn | GTG Val | GAC Asp | AAG Lys 10 | CCG Pro | CTC Leu | TTC Phe |
| ACC Thr | GCG Ala 15 | ACG Thr | TTC Phe | AAC Asn | GTC Val | CAG Gln 20 | GCC Ala | 108 |
| AGC Ser | TCC Ser | GCC Ala | GAC Asp 25 | TAC Tyr | GCC Ala | ACC Thr | TTC Phe |
| ATC Ile 30 | GCC Ala | GGC Gly | ATC Ile | CGC Arg | AAC Asn 35 | AAG Lys | CTC Leu | 156 |

| SEQUENCE DESCRIPTION: SEQ ID NO. 1 | | | | | | | |
|---|---|---|---|---|---|---|---|
| CGC Arg | AAC Asn | CCG Pro | GCG Ala | CAC His | TTC Phe | TCC Ser | CAC His 45 | |
| AAC Asn | CGC Arg | CCC Pro | GTG Val | CTG Leu 50 | CCG Pro | CCG Pro | GTC Val | 204 |
| GAG Glu | CCC Pro 55 | AAC Asn | GTC Val | CCG Pro | CCG Pro | AGC Ser 60 | AGG Arg | |
| TGG Trp | TTC Phe | CAC His | GTC Val 65 | GTG Val | CTC Leu | AAG Lys | GCC Ala | 252 |
| TCG Ser 70 | CCG Pro | ACC Thr | AGC Ser | GCC Ala | GGG Gly 75 | CTC Leu | ACG Thr | |
| CTG Leu | GCC Ala | ATT Ile 80 | CGG Arg | GCG Ala | GAC Asp | AAC Asn | ATC Ile 85 | 300 |
| TAC Tyr | CTG Leu | GAG Glu | GGC Gly | TTC Phe 90 | AAG Lys | AGC Ser | AGC Ser | |
| GAC Asp | GGC Gly | ACC Thr | TGG Trp | TGG Trp | GAG Glu | CTC Leu 100 | ACC Thr | 348 |

SEQUENCE DESCRIPTION: SEQ ID NO. 1

| CCG | GGC | CTC | ATC | CCC | GGC | GCC | ACC | |
|---|---|---|---|---|---|---|---|---|
| Pro | Gly | Leu | Ile 105 | Pro | Gly | Ala | Thr | |
| TAC | GTC | GGG | TTC | GGC | GGC | ACC | TAC | 396 |
| Tyr 110 | Val | Gly | Phe 115 | Gly | Gly | Thr | Tyr | |
| CGC | GAC | CTC | CTC | GGC | GAC | ACC | GAC | |
| Arg | Asp | Leu 120 | Leu | Gly | Asp | Thr | Asp 125 | |
| AAG | CTG | ACC | AAC | GTC | GCT | CTC | GGC | 444 |
| Lys | Leu | Thr | Asn | Val 130 | Ala | Leu | Gly | |
| CGG | CAG | CAG | CTG | GCG | GAC | GCG | GTG | |
| Arg | Gln 135 | Gln | Leu | Ala | Asp | Ala 140 | Val | |
| ACC | GCC | CTC | CAC | GGG | CGC | ACC | AAG | 492 |
| Thr | Ala | Leu | His 145 | Gly | Arg | Thr | Lys | |
| GCC | GAC | AAG | CCG | TCC | GGC | CCG | AAG | |
| Ala 150 | Asp | Lys | Pro | Ser | Gly 155 | Pro | Lys | |
| CAG | CAG | CAG | GCG | AGG | GAG | GCG | GTG | 540 |
| Gln | Gln | Gln 160 | Ala | Arg | Glu | Ala 165 | Val | |
| ACG | ACG | CTG | CTC | CTC | ATG | GTG | AAC | |
| Thr | Thr | Leu | Leu | Leu 170 | Met | Val | Asn | |
| GAG | GCC | ACG | CGG | TTC | CAG | ACG | GTG | 588 |
| Glu | Ala 175 | Thr | Arg | Phe | Gln | Thr 180 | Val | |
| TCT | GGG | TTC | GTG | GCC | GGG | TTG | CTG | |
| Ser | Gly | Phe | Val 185 | Ala | Gly | Leu | Leu | |
| CAC | CCC | AAG | GCG | GTG | GAG | AAG | AAG | 636 |
| His 190 | Pro | Lys | Ala | Val | Glu 195 | Lys | Lys | |
| AGC | GGG | AAG | ATC | GGC | AAT | GAG | ATG | |
| Ser | Gly | Lys 200 | Ile | Gly | Asn | Glu | Met 205 | |
| AAG | GCC | CAG | GTG | AAC | GGG | TGG | CAG | 684 |
| Lys | Ala | Gln | Val | Asn 210 | Gly | Trp | Gln | |
| GAC | CTG | TCC | GCG | GCG | CTG | CTG | AAG | |
| Asp | Leu 215 | Ser | Ala | Ala | Leu | Leu 220 | Lys | |
| ACG | GAC | GTG | AAG | CCT | CCG | CCG | GGA | 732 |
| Thr | Asp | Val | Lys 225 | Pro | Pro | Pro | Gly | |
| AAG | TCG | CCA | GCG | AAG | TTC | GCG | CCG | |
| Lys 230 | Ser | Pro | Ala | Lys | Phe 235 | Ala | Pro | |
| ATC | GAG | AAG | ATG | GGC | GTG | AGG | ACG | 780 |
| Ile | Glu | Lys 240 | Met | Gly | Val | Arg | Thr 245 | |
| GCT | GTA | CAG | GCC | GCC | AAC | ACG | CTG | |
| Ala | Val | Gln | Ala | Ala 250 | Asn | Thr | Leu | |
| GGG | ATC | CTG | CTG | TTC | GTG | GAG | GTG | 828 |
| Gly | Ile 255 | Leu | Leu | Phe | Val | Glu 260 | Val | |
| CCG | GGT | GGG | TTG | ACG | GTG | GCC | AAG | |
| Pro | Gly | Gly | Leu 265 | Thr | Val | Ala | Lys | |
| GCG | CTG | GAG | CTG | TTC | CAT | GCG | AGT | 876 |
| Ala 270 | Leu | Glu | Leu | Phe | His 275 | Ala | Ser | |
| GGT | GGG | AAA | TAGGTAGTTT | | TCCAGGTATA | | | |
| Gly | Gly | Lys 280 | | | | | | |
| CCTGCATGGG | | TAGTGTAAAA | | | GTCGAATAAA | | | 935 |
| CATGTCACAG | | AGTGACGGAC | | | TGATATAAAT | | | |
| AAATAAATAA | | ACGTGTCACA | | | GAGTTACATA | | | 995 |
| TAAACAAATA | | AATAAATAAT | | | TAAAAATGTC | | | |
| CAGTTTA | | | | | | | | 1032. |

2. A method according to claim 1 wherein the fusion product of the protein-synthesis inhibitor gene further comprises a gene coding for a ligand permitting the specific attachment of fungal cells.

3. Plants and plant parts which have a genotype modified by any one of claims 1 or 2.

4. A DNA transfer vector comprising an inserted DNA sequence according to any one of claims 1 or 2.

5. A DNA expression vector comprising an inserted DNA sequence according to any one of claims 1 or 2.

6. A method of preparing an agricultural preparation for inducing resistance of plants against fungi comprising the step of introducing a protein-synthesis inhibitor gene into a bacterial overproducer, wherein the protein-synthesis inhibitor gene comprises the following DNA sequence:

SEQUENCE DESCRIPTION: SEQ ID NO. 1

| | CTTAATAGCA GTCTTAGCTT | | | | CATCTTGTCC TGCATTACAT | | | |
|---|---|---|---|---|---|---|---|---|
| CC | ATG Met −1 | GCG Ala 1 | GCA Ala | AAG Lys | ATG Met | GCG Ala 5 | | 60 |
| AAG Lys | AAC Asn | GTG Val | GAC Asp | AAG Lys 10 | CCG Pro | CTC Leu | TTC Phe | |
| ACC Thr | GCG Ala 15 | ACG Thr | TTC Phe | AAC Asn | GTC Val | CAG Gln 20 | GCC Ala | 108 |
| AGC Ser | TCC Ser | GCC Ala | GAC Asp 25 | TAC Tyr | GCC Ala | ACC Thr | TTC Phe | |
| ATC Ile 30 | GCC Ala | GGC Gly | ATC Ile | CGC Arg | AAC Asn 35 | AAG Lys | CTC Leu | 156 |
| CGC Arg | AAC Asn | CCG Pro | GCG Ala | CAC His | TTC Phe | TCC Ser | CAC His 45 | |
| AAC Asn | CGC Arg | CCC Pro | GTG Val | CTG Leu 50 | CCG Pro | CCG Pro | GTC Val | 204 |
| GAG Glu | CCC Pro 55 | AAC Asn | GTC Val | CCG Pro | CCG Pro | AGC Ser 60 | AGG Arg | |
| TGG Trp | TTC Phe | CAC His | GTC Val 65 | GTG Val | CTC Leu | AAG Lys | GCC Ala | 252 |
| TCG Ser 70 | CCG Pro | ACC Thr | AGC Ser | GCC Ala | GGG Gly 75 | CTC Leu | ACG Thr | |
| CTG Leu | GCC Ala | ATT Ile 80 | CGG Arg | GCG Ala | GAC Asp | AAC Asn | ATC Ile 85 | 300 |
| TAC Tyr | CTG Leu | GAG Glu | GGC Gly | TTC Phe | AAG Lys | AGC Ser | AGC Ser | |

SEQUENCE DESCRIPTION: SEQ ID NO. 1

| | | | | 90 | | | | |
|---|---|---|---|---|---|---|---|---|
| GAC | GGC | ACC | TGG | TGG | GAG | CTC | ACC | 348 |
| Asp | Gly | Thr | Trp | Trp | Glu | Leu 100 | Thr | |
| CCG | GGC | CTC | ATC | CCC | GGC | GCC | ACC | |
| Pro | Gly | Leu | Ile 105 | Pro | Gly | Ala | Thr | |
| TAC | GTC | GGG | TTC | GGC | GGC | ACC | TAC | 396 |
| Tyr 110 | Val | Gly | Phe | Gly 115 | Gly | Thr | Tyr | |
| CGC | GAC | CTC | CTC | GGC | GAC | ACC | GAC | |
| Arg | Asp | Leu 120 | Leu | Gly | Asp | Thr | Asp 125 | |
| AAG | CTG | ACC | AAC | GTC | GCT | CTC | GGC | 444 |
| Lys | Leu | Thr | Asn | Val 130 | Ala | Leu | Gly | |
| CGG | CAG | CAG | CTG | GCG | GAC | GCG | GTG | |
| Arg | Gln 135 | Gln | Leu | Ala | Asp | Ala 140 | Val | |
| ACC | GCC | CTC | CAC | GGG | CGC | ACC | AAG | 492 |
| Thr | Ala | Leu | His 145 | Gly | Arg | Thr | Lys | |
| GCC | GAC | AAG | CCG | TCC | GGC | CCG | AAG | |
| Ala 150 | Asp | Lys | Pro | Ser | Gly 155 | Pro | Lys | |
| CAG | CAG | CAG | GCG | AGG | GAG | GCG | GTG | 540 |
| Gln | Gln | Gln 160 | Ala | Arg | Glu | Ala 165 | Val | |
| ACG | ACG | CTG | CTC | CTC | ATG | GTG | AAC | |
| Thr | Thr | Leu | Leu | Leu 170 | Met | Val | Asn | |
| GAG | GCC | ACG | CGG | TTC | CAG | ACG | GTG | 588 |
| Glu | Ala 175 | Thr | Arg | Phe | Gln | Thr 180 | Val | |
| TCT | GGG | TTC | GTG | GCC | GGG | TTG | CTG | |
| Ser | Gly | Phe | Val 185 | Ala | Gly | Leu | Leu | |
| CAC | CCC | AAG | GCG | GTG | GAG | AAG | AAG | 636 |
| His 190 | Pro | Lys | Ala | Val | Glu 195 | Lys | Lys | |
| AGC | GGG | AAG | ATC | GGC | AAT | GAG | ATG | |
| Ser | Gly | Lys | Ile | Gly | Asn | Glu | Met | |

| | | 200 | | | | 205 | | |
|---|---|---|---|---|---|---|---|---|
| AAG | GCC | CAG | GTG | AAC | GGG | TGG | CAG | 684 |
| Lys | Ala | Gln | Val | Asn 210 | Gly | Trp | Gln | |
| GAC | CTG | TCC | GCG | GCG | CTG | CTG | AAG | |
| Asp | Leu 215 | Ser | Ala | Ala | Leu | Leu 220 | Lys | |
| ACG | GAC | GTG | AAG | CCT | CCG | CCG | GGA | 732 |
| Thr | Asp | Val | Lys 225 | Pro | Pro | Pro | Gly | |
| AAG | TCG | CCA | GCG | AAG | TTC | GCG | CCG | |
| Lys 230 | Ser | Pro | Ala | Lys | Phe 235 | Ala | Pro | |
| ATC | GAG | AAG | ATG | GGC | GTG | AGG | ACG | 780 |
| Ile | Glu | Lys 240 | Met | Gly | Val | Arg | Thr 245 | |
| GCT | GTA | CAG | GCC | GCC | AAC | ACG | CTG | |
| Ala | Val | Gln | Ala | Ala 250 | Asn | Thr | Leu | |
| GGG | ATC | CTG | CTG | TTC | GTG | GAG | GTG | 828 |
| Gly | Ile 255 | Leu | Leu | Phe | Val | Glu 260 | Val | |
| CCG | GGT | GGG | TTG | ACG | GTG | GCC | AAG | |
| Pro | Gly | Gly | Leu 265 | Thr | Val | Ala | Lys | |
| GCG | CTG | GAG | CTG | TTC | CAT | GCG | AGT | 876 |
| Ala 270 | Leu | Glu | Leu | Phe | His 275 | Ala | Ser | |
| GGT | GGG | AAA | TAGGTAGTTT | | | TCCAGGTATA | | |
| Gly | Gly | Lys 280 | | | | | | |
| CCTGCATGGG | | | TAGTGTAAAA | | | GTCGAATAAA | | 935 |
| CATGTCACAG | | | AGTGACGGAC | | | TGATATAAAT | | |
| AAATAAATAA | | | ACGTGTCACA | | | GAGTTACATA | | 995 |
| TAAACAAATA CAGTTTA | | | AATAAATAAT | | | TAAAAATGTC | | |
| | | | | | | | | 1032. |

\* \* \* \* \*

UNITED STATES PATENT AND TRADEMARK OFFICE
CERTIFICATE OF CORRECTION

PATENT NO. : 5,633,442
DATED : May 27, 1997
INVENTOR(S) : Schell, et al.

It is certified that error appears in the above-identified patent and that said Letters Patent is hereby corrected as shown below:

1st page, 2nd col., line 11, "113:12772" should read --113:127723--

Col. 5, line 22, "F'(lacI$_L^p$" should read --F'(laci$^q$--

Col. 9, line 66, "wund" should read --wunl--

Col. 10, line 34, "in tact" should read --intact--

Col. 17, line 25, "165" should appear under last column, not penultimate column

Col. 19, line 29, "165" should appear under last column, not penultimate column

Signed and Sealed this

Third Day of February, 1998

BRUCE LEHMAN

*Attest:*

*Attesting Officer*  *Commissioner of Patents and Trademarks*